United States Patent
Shao

(10) Patent No.: US 10,043,297 B2
(45) Date of Patent: Aug. 7, 2018

(54) METHOD AND SYSTEM FOR MANAGING IMAGING DATA

(75) Inventor: Lingxiong Shao, Saratoga, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 624 days.

(21) Appl. No.: 13/991,264

(22) PCT Filed: Nov. 25, 2011

(86) PCT No.: PCT/IB2011/055296
§ 371 (c)(1),
(2), (4) Date: Jun. 3, 2013

(87) PCT Pub. No.: WO2012/077012
PCT Pub. Date: Jun. 14, 2012

(65) Prior Publication Data
US 2013/0249941 A1    Sep. 26, 2013

Related U.S. Application Data

(60) Provisional application No. 61/420,356, filed on Dec. 7, 2010.

(51) Int. Cl.
*G06T 11/60* (2006.01)
*G06F 19/00* (2018.01)

(52) U.S. Cl.
CPC ............ *G06T 11/60* (2013.01); *G06F 19/321* (2013.01)

(58) Field of Classification Search
None
See application file for complete search history.

(56) References Cited

U.S. PATENT DOCUMENTS

| | | | |
|---|---|---|---|
| 6,347,329 B1* | 2/2002 | Evans | G06F 19/322 705/2 |
| 7,545,967 B1* | 6/2009 | Prince | G06T 5/50 128/920 |
| 7,607,079 B2 | 10/2009 | Reiner | |
| 2006/0061595 A1 | 3/2006 | Goede et al. | |
| 2008/0059238 A1* | 3/2008 | Park | G06F 19/321 705/3 |
| 2008/0144897 A1 | 6/2008 | Lal et al. | |

(Continued)

FOREIGN PATENT DOCUMENTS

| | | | |
|---|---|---|---|
| JP | 2008108079 A | 5/2008 | |
| WO | 02098822 A2 | 12/2002 | |

OTHER PUBLICATIONS

Catlin et al. (Timothy Catlin et al., "InterNote: Extending a Hypermedia Framework to Support Annotative Collaboration", Hypertext '89 Proceedings of the second annual ACM conference on Hypertext, pp. 365-378, ACM, New York, NY, USA, 1989).*

(Continued)

*Primary Examiner* — William A Beutel

(57) ABSTRACT

A method and system for managing imaging data are provided. In one aspect, imaging data is stored in combination with user-generated information relating to the imaging data. In various other aspects, an image file header structure including user-generated information, a software editing tool to record user-generated information, and an imaging display tool to correlate imaging data and user-generated information are provided.

3 Claims, 5 Drawing Sheets

(56) References Cited

U.S. PATENT DOCUMENTS

| | | | |
|---|---|---|---|
| 2009/0092953 A1* | 4/2009 | Yang | G09B 19/24 |
| | | | 434/219 |
| 2009/0292559 A1* | 11/2009 | Ranjan | G06F 19/321 |
| | | | 705/3 |
| 2011/0109650 A1* | 5/2011 | Kreeger | G06F 19/3406 |
| | | | 345/634 |
| 2011/0153351 A1* | 6/2011 | Vesper | G06Q 50/22 |
| | | | 705/2 |

OTHER PUBLICATIONS

3D-Doctor Related News; www.ablesw.com/3d-doctor/news.html. pp. 1-9 (printed Sep. 2010).

Brill, A. B., et al.; Display Systems in Nuclear Medicine; 1978; Seminars in Nuclear Medicine; vol. VIII, No. 2; pp. 155-161.

Crass, J. R., et al.; Radiologic Application of a Mecrocomputer-Based Three-Dimensional Imaging System; 1992; AJR; 158:673-674.

Goitein, M., et al.; Multi-Dimensional Treatment Planning: I. Delineation of Anatomy; 1983; Int'l J. Radiation Oncology Biol. Phys.; 9:777-787.

Image Technology Laboratories; WarpSpeed Product Line; www.imagetechlabs.com/product/html pp.1-6; printed Sep. 2010.

Mildenberger, P., et al.; Introduction to the DICOM standard; 2002; Eur. Radiol.; 12:920-927.

Robertson, I. D., et al.; Hospital, Radiology, and Picture Archiving and Communication Systems; 2008; Veterinary Radiology and Ultrasound; 49(1)S19-S28.

\* cited by examiner

METHOD AND SYSTEM FOR MANAGING IMAGING DATA

The present application relates generally to the imaging arts and more particularly to a method and system for managing imaging data. The application subject matter finds particular use in connection with medical imaging systems such as for example computed tomography (CT) imaging systems, single photon emission computed tomography (SPECT) imaging systems, positron emission tomography (PET) imaging systems, x-ray imaging systems, other imaging systems, and combinations thereof. However, in its broader aspects, the application subject matter is not limited to the medical imaging field, and may apply in other fields such as for example imaging for security purposes in airports or other checkpoints. These and similar imaging systems typically gather imaging data regarding an object, such as a human person, and record that imaging data for later analysis and use. Such uses include for example medical diagnosis, tracking the growth or properties of a tumor within a person's body, looking for illegal or dangerous items such as guns and knives for security purposes, and the like. Thus, while the preferred embodiment is medical imaging and much of the following description relates to that field, the present invention applies in other fields as well.

In most image reconstruction, processing, analysis, and visualization applications, images are generated and recorded for a specific reason or reasons. Often these images are made in connection with an investigation, such as determining whether a patient has cancer, or determining the extent of a cancer, or determining whether a bone has been broken, or determining whether an organ is functioning properly. Many times, making such determinations involves the opinion(s) of one or more trained professionals such as physicians, radiologists, and the like, after review of the imaging data. In the past, the analysis and conclusions of such persons have typically been recorded in a writing or in a recorded audio dictation which is stored separately from the imaging data itself.

According to one aspect of the present invention, imaging data is stored in combination with user-generated information relating to the imaging data. The method comprises, in various aspects, an image file header structure including user-generated information, a software editing tool to record user-generated information, and an imaging display tool to correlate imaging data and user-generated information. Each one of these and other aspects of the present invention may be used alone or in combination with other aspects of the present invention.

Numerous advantages and benefits will become apparent to those of ordinary skill in the art upon reading the following detailed description of the preferred embodiments. The invention may take form in various components and arrangements of components, and in various process operations and arrangements of process operations. The drawings are only for the purpose of illustrating preferred embodiments and are not to be construed as limiting the invention.

Figure 1:
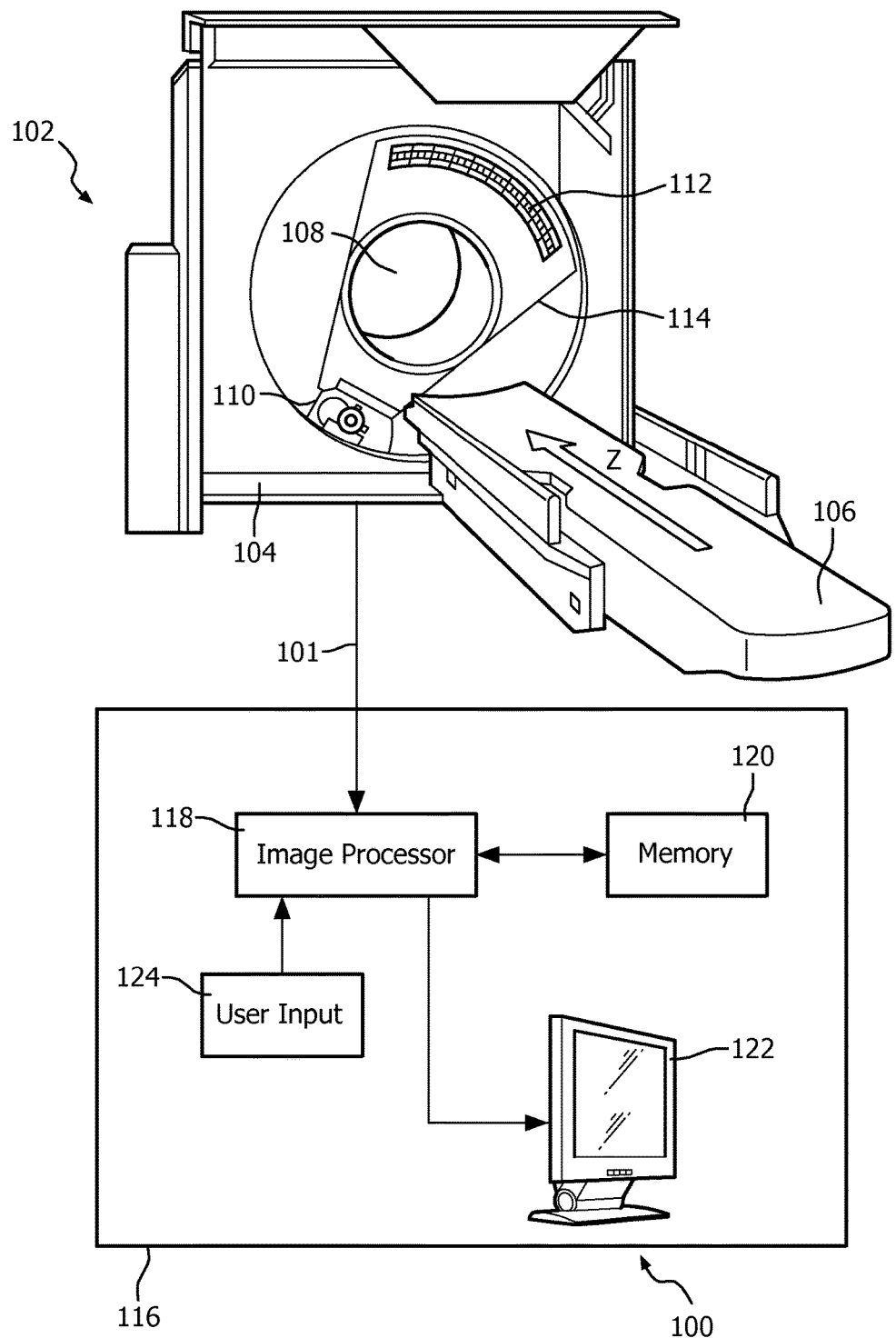
FIG. 1 is an exemplary CT imaging system, with a portion of the stationary gantry cut away to reveal the rotating x-ray source and data measurement system within the gantry.

The subject matter of the present disclosure finds use in connection with any imaging system, for example, a CT imaging system. More specifically, with reference to FIG. 1, in an exemplary embodiment the imaging system 100 is a medical CT imaging system. A CT imaging acquisition system 102 includes a gantry 104 and an object support 106 such as a table or couch which moves along the z-axis. A patient or other object to be imaged (not shown) lies or is placed down on the object support 106 and is moved to be disposed within an aperture 108 in the gantry 104. Once the patient or object is in position within the aperture 108, an x-ray source 110 emits a projection of x-rays to be gathered by an x-ray data measurement system 112 inside the gantry 104. (A portion 114 of the gantry 104 is cut away in FIG. 1 to show the x-ray source 110 and x-ray data measurement system 112 which are housed inside the gantry 104.) The x-ray source 110 and data measurement system 112 rotate together around the aperture 108 to record CT imaging data from various positions. In some embodiments such rotation may occur while the object support 106 is stationary. In other embodiments such rotation may occur in conjunction with linear movement of the object support 106 along the z-axis in a "helical" scan. The rotation is possible because the x-ray source 110 and the data measurement system 112 are each mounted to a common rotor (not shown) inside the gantry 104.

The data measurement system 112 of the CT imaging acquisition system 102 thus acquires CT imaging data in the form of detected x-rays. The system 102 then transfers the acquired CT imaging data on to a CT imaging, processing and display system 116 through a communication link 101. Although the systems 102 and 116 are shown and described here as being separate systems for purposes of illustration, they may in other embodiments be part of a single system. When the systems 102 and 116 are separate systems, the communication link 101 may be any link which permits the transfer of data between the systems, such as a Local Area Network, the Internet, a physical transfer of a memory storage medium such as a computer diskette, CD-ROM, or flash drive, or the like. The communication link 101 may be wired, wireless, or a combination thereof. Thus, the systems 102 and 116 may be located in different rooms, different buildings, or even different cities.

Via the communication link 101, the acquired CT imaging data passes to an image processor 118 which stores the acquired CT imaging data in a memory 120. The image processor 118 applies well-known image reconstruction techniques to electronically process the acquired CT imaging data and generate reconstructed imaging data, comprising images of the imaged patient or other object. The image processor 118 can show the resulting reconstructed imaging data on an associated display 122. A user input 124 such as a keyboard and/or mouse device may be provided for a user to control the processor 122.

The imaging system 100 may be a stand-alone unit which provides only CT-based imaging, as is shown in FIG. 1. Although not shown here, the imaging system 100 may additionally include appropriate components for PET and/or SPECT imaging, or some other imaging modality, in conjunction with the CT-based imaging components. Also, although the exemplary system of FIG. 1 is a CT imaging system, the present method also applies to many other imaging systems such as PET systems, SPECT systems, MRI systems, and combinations thereof. All such systems have an imaging acquisition component (such as the CT system 102) and an imaging processing component (such as the CT system 116). The imaging acquisition component generates, measures and records one or more different kinds of acquired imaging data concerning an imaged subject. The imaging processing component receives the acquired imaging data and in some cases processes it to generate reconstructed imaging data which can be viewed on a display. In other cases, such post-acquisition processing may not be necessary in order to display the imaging data for review by users.

In many instances, it is desirable for the imaging data to be transferred to yet other computer systems for review, consideration and perhaps manipulation by many different users. These users may be located in many different locations, and may use many different kinds of computer systems to view the imaging data. For example, in the particular context of medical imaging data, several medical professionals with differing kinds of expertise may need to see the imaging data in order for the patient to make medical decisions in consultation with a primary care physician. The transfer of imaging data may be accomplished through any type of communication link, such as the examples discussed above in connection with the communication link 101. It is this storage and transfer of imaging data from one computer system to another that is the subject matter of the present disclosure.

Thus the functions described herein can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory such as memory 120, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic shown and described herein preferably resides in or on a computer readable medium such as the memory 120. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

The present disclosure provides a method and system for managing user-generated information concerning imaging data. User-generated information is herein defined as information which is generated by a user and based at least in part on the user's review of imaging data. Two exemplary kinds of user-generated information are diagnostic information and technical information.

Diagnostic user-generated information is herein defined as any conclusion, opinion, observation, or question generated by a user concerning the imaged subject after review of the imaging data. In the medical imaging field, diagnostic user-generated information might be whether a patient does or does not have cancer or some other disease or condition. And, if cancer is determined to be present, it might also include the location, size or other characteristic(s) of cancerous tumors in the patient's body. As another example, in the security imaging field, diagnostic user-generated information might include whether a person passing through a security check point has a weapon, contraband, or the like. Diagnostic user-generated information can additionally include information about the diagnostic process, such as who made the diagnosis, the conditions under which the diagnosis was made, where it was made, and when it was made. It might further include yet other information, such as chemical or non-imaging diagnostic test results relating to the imaged subject upon which the user relied in conjunction with the imaging data to make the diagnosis.

Technical user-generated information is herein defined as any conclusion, opinion, observation, or question generated by a user concerning the imaging data or the imaging process after review of the imaging data. For example, the user might question whether a particular location in the imaging data contains an undesirable imaging artifact resulting from the image reconstruction process. Or, the imaging technologist who operated the imaging equipment to generate the acquired imaging data may record problems or abnormalities in the imaging data, noting potential cause(s) from the data acquisition process. The essential difference between diagnostic and technical information, as those terms are defined herein, is that diagnostic information is directed to the imaged subject, while technical information is directed to the reconstructed imaging data or the imaging process.

Figure 2:
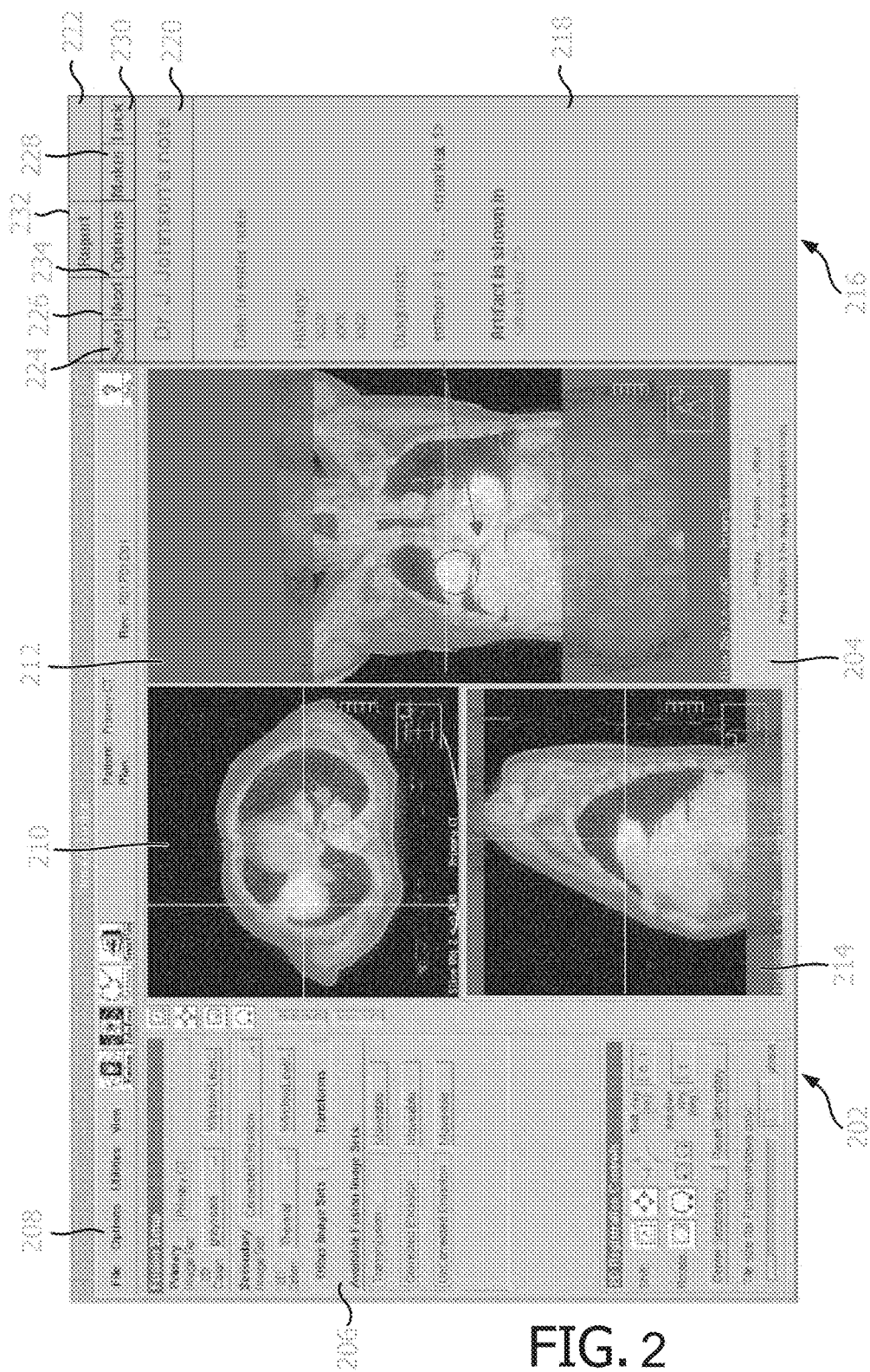
FIG. 2 shows an image display tool in combination with a user record tool.

Because user-generated information is based at least in part on the user's review of the imaging data, it may be conveniently stored in combination with the imaging data. An exemplary embodiment is illustrated in FIG. 2. As shown there, an image display tool 202 includes an image display portion 204, an image control panel portion 206, and a menu portion 208.

The image display portion 204 contains the three standard medical image views of reconstructed imaging data: a transverse plane view 210, a coronal plane view 212, and a sagittal plane view 214. One horizontal line and one vertical line in each of the three views 210, 212 and 214 illustrate the respective orientations of the three views; the intersection point of the lines in each view is the only point common to all three views.

The image control panel portion 206 contains various options for the user to display imaging data in the image display portion 204. A user may use the control panel portion 206 to choose what imaging data to display (e.g. CT, PET, or both), the location of the three imaging planes 210, 212 and 214 within the displayed reconstructed imaging data, whether to use color or grayscale, and the like.

The menu portion 208 contains other options for the user to manipulate the imaging data displayed in the image display portion 204. Thus, a user may use the menu portion 208 to upload an identified acquired or reconstructed set of imaging data, or to copy selected images for export, and the like.

FIG. 2 also illustrates another window next to the image display tool 202. This is an exemplary user record tool 216, which may be employed by a user to record user-generated information such as diagnostic information or technical information. Thus, in the exemplary embodiment of FIG. 2, the user record tool 216 includes a record portion 218, a title portion 220, and a menu portion 222. While this configuration is useful, other configurations are of course possible.

A user may use the record portion 218 to enter, record and review user-generated information in a record. One or more user-generated information records may conveniently be stored in combination with the file that stores the imaging data illustrated and manipulated by the image display tool 202. These records are preferably stored in the same file as the imaging data, but they may alternatively be stored in a separate file or files which are stored and transferred along with the imaging data file. A user-generated information record may be a simple text record containing the user's notes. Alternatively, the user-generated information record or portions thereof may follow pre-defined formats, such as check box options, radio button options, drop-down lists, or other known graphical user interface formats. Moreover, the user-generated information record may conform to any one of several medical diagnostic forms known within particular areas of practice, which specify questions to be answered or information to be provided. The record may even contain an audio file recording a user's orally dictated notes, optionally with a software tool to encode and/or decode the voice file.

Figure 3:
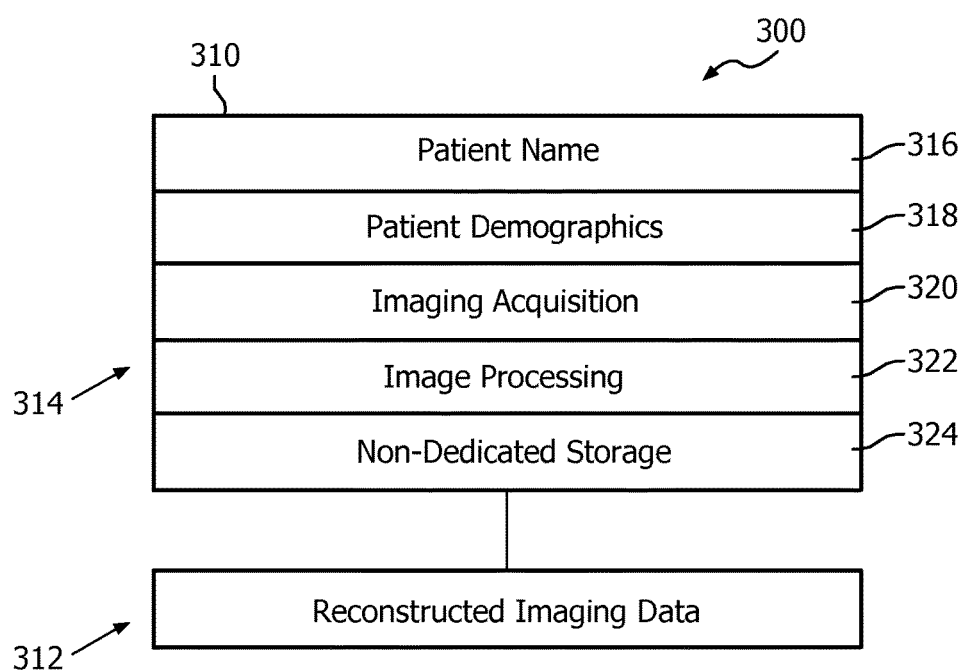
FIG. 3 is a schematic illustration of a conventional DICOM image file format.

In a particularly preferred embodiment, the present invention is used in conjunction with the Digital Imaging and Communications in Medicine ("DICOM") standard created by the National Electrical Manufacturers Association. The DICOM standard aims to facilitate the storage, distribution and viewing of reconstructed medical images such as CT images, PET images, SPECT images, MRI images, and the like. DICOM is the most common standard for storing, transmitting and receiving medical imaging data in use today. The DICOM standard defines an imaging file format. FIG. 3 is a schematic illustration of the conventional DICOM file format 300. Pursuant to the DICOM image file format 300, a single DICOM file 310 contains an imaging data portion 312 and a header portion 314. The imaging data portion 312 stores the imaging data, i.e., the two-dimensional or three-dimensional matrix of intensity or other values which define a pixilated or voxelated image. The header portion 314 stores information related to the imaging data portion 312. Other file formats use a similar header/image data format.

The information stored in the header portion 314 might include, for example, the name of the patient 316 being imaged. The header portion 314 also might include demographic information 318 concerning the patient, such as for example birth date, height, weight, sex, and the like. The header portion 314 also might include image acquisition information 320 concerning the imaging data 312, such as for example the type of imaging scan performed (CT, PET, etc.), the duration of the imaging acquisition, the current applied to the x-ray tube for a transmission x-ray imaging acquisition, the type of radiopharmaceutical used for an emission imaging acquisition, the pixel or voxel matrix size of the reconstructed imaging data, and the like. The header portion 314 also might include image processing information 322, concerning how the acquired imaging data was processed to generate reconstructed imaging data sorted in portion 312. Under the DICOM standard, the header portion 314 also includes a portion of non-dedicated or free memory 324 which may be used by a particular user to store any information defined by that user. In that way, the DICOM standard permits some limited user customization to the types of information stored in the header portion 314.

Thus, when used in conjunction with the DICOM standard illustrated in FIG. 3, the user-generated information records discussed above may be stored in the non-dedicated memory 324 of the header portion 314. This is shown, for example, in FIG. 4 which includes several user-generated information records 402 stored in the non-dedicated memory 324. Standardized imaging file formats other than DICOM also may incorporate similar non-dedicated memory portions which may be utilized to store the user-generated information records entered by users. If not, such information may be stored in a separate file from the imaging data file, such that the separate files are stored and transferred together.

Returning to the description of FIG. 2, the title portion 220 of the user record tool 216 identifies the user-generated information record which appears in the record portion 218. Thus, the title may identify the user who authored the record, and/or identify the information entered into the record.

The menu portion 222 of the user record tool 216 provides various options for manipulating user-generated information records. Thus, in the representative example of FIG. 2, the user may save 224 the user-generated information record which appears in the record portion 218. Or, if there are several such user-generated information records, as discussed further below, the user may choose to view the next 226 record. The user may add a marker 228 in the record portion 218, as described further below. The user may lock 230 his or her own user-generated information record, meaning that while other users may view that record, other users may not modify that record. The user may generate a report 232, as described further below. Various other options 234 may also be provided.

To enhance the usefulness of a user-generated information record, the user may add a marker to a portion or portions of the imaging data as being a region of interest. For example, the user may identify a portion of the imaging data which corresponds to a cancerous tumor. Or, the user may identify a portion of the imaging data which may contain an undesirable imaging artifact. In such an event, the user may use a mouse or other pointing device to define the location and extent of the region of interest in the image display portion 204, as is known in the art. It is also well known for an automated search tool to identify candidate regions of interest in the imaging data for review and final designation by a medical professional. Then the user may insert a marker link in the user-generated information record portion 218 to that region of interest, for example by choosing the marker tab 228 in the menu portion 222. This can conveniently be done immediately in conjunction with identifying the region of interest. In this way, subsequent reviewers of the user-generated information record can click on the marker in the user-generated information record, and the image display tool 202 will then show the corresponding region of interest in all three planes 210, 212 and 214 of the reconstructed imaging data in the image display portion 204.

The report command 232 generates a new export report file, such as a .doc, .pdf or .txt file, containing a formatted summary of one or more of the user-generated information records. The exported report may contain the written user-generated information or portions thereof, copies of portions of the imaging data, and other information. In this way the user-generated information records may be transmitted to and reviewed by a person who does not have the software which runs the tools 202, 216. For example, exported files may be convenient for transmitting the user-generated information or portions thereof to a primary care physician.

Many different users may need or desire to enter a user-generated information record. For example, one or more technologists operate the imaging system to generate the acquired imaging data, and also to process the acquired imaging data to generate reconstructed imaging data. These technologists are qualified by their education, training and experience to operate the imaging system and manipulate the imaging data. However, they are not necessarily qualified to interpret the medical significance of the imaging data. During the imaging acquisition and reconstruction processes, a technologist may nonetheless encounter a problem or observe an abnormality that he or she wishes to communicate to the medical professional(s) who will later be reviewing the reconstructed imaging data to determine its medical significance. In that event, the technologist may review the imaging data and, if it appears that there may be a problem with the data, create a user-generated information report for review and consideration by the medical professional(s).

Figure 4:
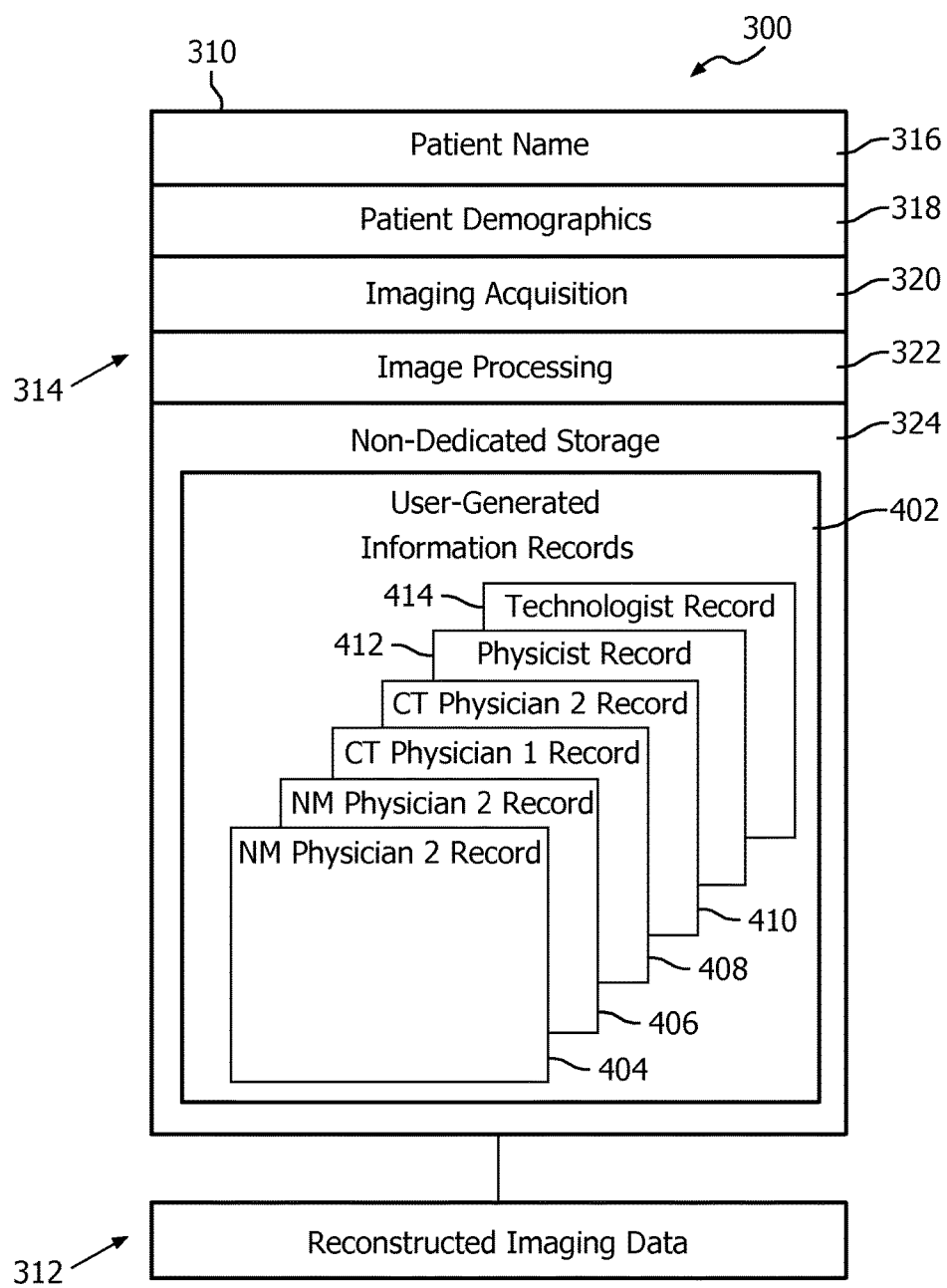
FIG. 4 is a schematic illustration of an exemplary image file format in accordance with the present disclosure.

Another group of users are the medical professionals who review the imaging data to determine its medical significance. This group of users includes various physicians, radiologists, and the like, many of whom have very specialized areas of expertise. Depending on the particular circumstances, a given set of imaging data may need to be reviewed by more than one medical professional in order to make a complete and reliable medical diagnosis and, if needed, a plan for treatment. For example, in SPECT/CT imaging, quite often the reconstructed imaging data will be reviewed by both a SPECT specialist and a CT specialist. It is also not uncommon for two professionals within the same field of expertise to review the same imaging data, in order to gain the benefit of a second opinion. Thus each one of several medical professionals may desire to enter a user-generated record containing his or her own conclusions concerning the imaging data. This is illustrated in FIG. 4, for example, in which the user-generated information records include a first nuclear medicine physician's record 404, a second nuclear medicine physician's record 406, a first CT physician's record 408, a second CT physician's record 410, a physicist's record 412, and a technologist's record 414.

Indeed, in many cases, user-generated information may be partly based on other user-generated information. It is not uncommon for example for a primary care physician to review reports from other physicians such as a nuclear medicine physician and a CT physician before generating a final omnibus report. Thus, each record 402 may contain marker links not only to regions of interest in the imaging data, but also to other records 402 or even portions of other records 402. To facilitate such embodiments, the imaging data and associated user-generated information may be stored at one location for access by all users. One example is a PACS (picture archiving and communication system). Such access may be granted via the Internet or other communication networks allowing a wide distribution.

Figure 5:
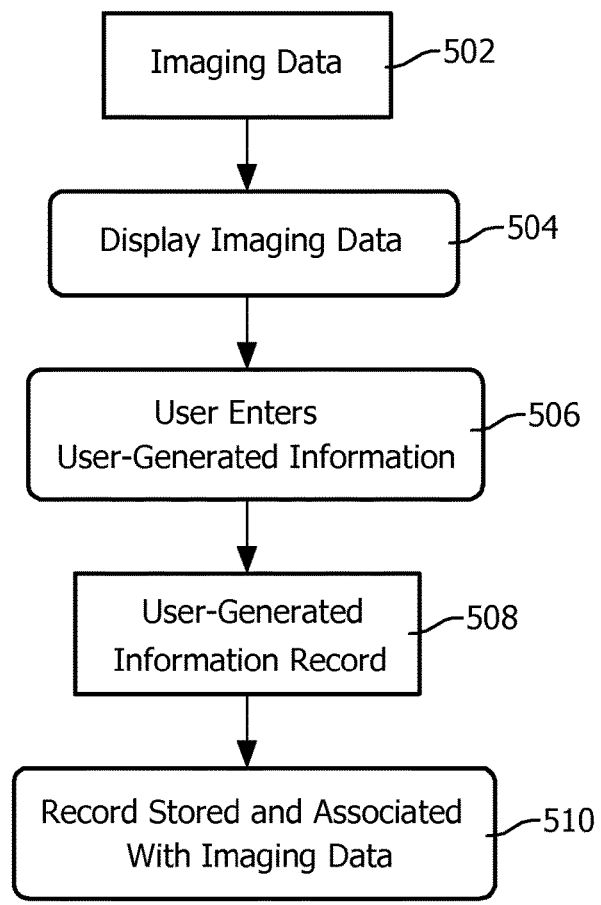
FIG. 5 illustrates an exemplary method for combining imaging data with user-generated information.

Thus a method for combining imaging data with user-generated information relating to the imaging data is provided. An exemplary such method 500 is illustrated in FIG. 5. The method 500 starts with imaging data 502. The imaging data 502 may include imaging data directly acquired by an imaging system, or imaging data which has been reconstructed or otherwise generated from originally acquired imaging data, or combinations thereof. The imaging data 502 is displayed 504 for review by a user. The user then enters 506 user-generated information concerning the imaging data 502. The user-generated information is stored in a record 508 which is associated with the imaging data so that the imaging data 502 and the user-generated information record 510 are stored and transferred together.

The invention has been described with reference to the preferred embodiments. Obviously, modifications and alterations will occur to others upon reading and understanding the preceding detailed description. For example, a privacy protection feature may be added to the user record tool 216. With this feature, the user may prevent any user other than specified individuals or specified classes of individuals from accessing the user-generated information record, or portions thereof. For example, this feature may be used to prevent transfer of confidential patient information to imaging system vendors, yet still allow transfer of some data for help in problem-solving concerning the imaging system equipment. It is intended that the invention be construed as including all such modifications and alterations insofar as they come within the scope of the appended claims or the equivalents thereof. The invention may take form in various compositions, components and arrangements, combinations and sub-combinations of the elements of the disclosed embodiments.

Having thus described the preferred embodiments, the invention is now claimed to be:

1. A method for combining imaging data with user-generated information relating to the imaging data, the method comprising:
    generating a user interface on a display of an imaging system comprising an image processor, wherein generating the user interface comprises:
    generating a first window comprising an image display tool; and generating a second window comprising a user record tool; wherein the first window and the second window are displayed separately and concurrently;
    providing the imaging data in an image display portion of the image display tool; recording user-generated information concerning the imaging data in a record portion of the user record tool entered by a first user via a user input operatively connected to the imaging system, wherein the user-generated information comprises a first marker link to another record of user-generated information concerning the imaging data entered by a second user and a second marker link to a region of interest within the imaging data; and
    storing a record of the user-generated information, and associating the record with the imaging data so that the imaging data and the user-generated information record are stored and transferred together.

2. An imaging system for combining imaging data with user-generated information relating to the imaging data, the imaging system comprising an image processor, a display operatively connected to the image processor, and software embodied on a tangible medium and readable by the image processor, the software comprising logic to:
- generate a user interface on the display, wherein generating the user interface comprises:
- generating a first window comprising an image display tool; and
- generating a second window comprising a user record tool;
- wherein the first window and the second window are displayed separately and concurrently;
- provide the imaging data in an image display portion of the image display tool;
- record user-generated information concerning the imaging data in a record portion of the user record tool entered by a first user via a user input operatively connected to the image processor, wherein the user-generated information comprises a first marker link to another record of user-generated information concerning the imaging data entered by a second user;
- provide a second marker link between the user-generated information and a region of interest within the imaging data; and
- store a record of the user-generated information, and associate the record with the imaging data so that the imaging data and the user-generated information record are stored and transferred together.

3. An imaging system for combining reconstructed image data with user-generated information relating to reconstructed imaging data, the imaging system comprising an image processor, a display operatively connected to the image processor, and software embodied on a tangible medium and readable by the image processor, the software comprising logic to:
- reconstruct an acquired imaging data to generate the reconstructed imaging data;
- generate a user interface on the display, wherein generating the user interface comprises:
- generating a first window comprising an image display tool; and
- generating a second window comprising a user record tool;
- wherein the first window and the second window are displayed separately and concurrently;
- provide the reconstructed imaging data in an image display portion of the image display tool;
- record user-generated information concerning the reconstructed imaging data in a record portion of the user record tool entered by a first user via a user input operatively connected to the image processor, wherein the user-generated information comprises a first marker link to another record of user-generated information concerning the imaging data entered by a second user;
- provide a second marker link between the user-generated information and a region of interest within the reconstructed imaging data; and
- store a record of the user-generated information, and associate the record with the reconstructed imaging data so that the reconstructed imaging data and the user-generated information record are stored and transferred together.

* * * * *